United States Patent [19]

Williams

[11] Patent Number: 5,707,385

[45] Date of Patent: Jan. 13, 1998

[54] DRUG LOADED ELASTIC MEMBRANE AND METHOD FOR DELIVERY

[75] Inventor: Michael S. Williams, Chapel Hill, N.C.

[73] Assignee: Advanced Cardiovascular Systems, Inc., Santa Clara, Calif.

[21] Appl. No.: 340,717

[22] Filed: Nov. 16, 1994

[51] Int. Cl.⁶ .................................................. A61M 29/00
[52] U.S. Cl. .............. 606/192; 606/198; 604/96; 604/104; 623/12
[58] Field of Search .................. 604/96, 104, 171, 604/264, 265, 280, 282; 606/1, 108, 190–194, 198; 623/1, 11, 12

[56] References Cited

U.S. PATENT DOCUMENTS

| | | |
|---|---|---|
| 4,346,028 | 8/1982 | Griffith . |
| 4,417,576 | 11/1983 | Baran ........................... 604/101 X |
| 4,423,725 | 1/1984 | Baran et al. .................. 604/101 X |
| 4,633,873 | 1/1987 | Dumican et al. . |
| 4,718,907 | 1/1988 | Karwoski et al. . |
| 4,722,335 | 2/1988 | Vilasi . |
| 4,723,549 | 2/1988 | Wholey et al. . |
| 4,732,152 | 3/1988 | Wallsten et al. . |
| 4,733,665 | 3/1988 | Palmaz . |
| 4,739,762 | 4/1988 | Palmaz . |
| 4,768,507 | 9/1988 | Fischell et al. . |
| 4,776,337 | 10/1988 | Palmaz . |
| 4,816,339 | 3/1989 | Tu et al. . |
| 4,877,030 | 10/1989 | Beck et al. . |
| 4,878,906 | 11/1989 | Lindemann et al. . |
| 4,879,135 | 11/1989 | Greco et al. . |
| 4,902,289 | 2/1990 | Yannas ................................ 623/1 |
| 4,994,033 | 2/1991 | Shockey et al. ..................... 604/101 |
| 5,059,211 | 10/1991 | Stack et al. . |

(List continued on next page.)

FOREIGN PATENT DOCUMENTS

| | | |
|---|---|---|
| 567 788 A1 | 11/1993 | European Pat. Off. . |
| 604 022 A1 | 6/1994 | European Pat. Off. . |
| 621 017 A1 | 10/1994 | European Pat. Off. . |
| 649 5/637 A1 | 4/1995 | European Pat. Off. . |
| 3640 745 A1 | 6/1987 | Germany . |
| WO 91/17789 | 11/1991 | WIPO . |
| WO 93/06792 | 4/1993 | WIPO . |

OTHER PUBLICATIONS

"Fiber–Reinforced Absorbable Composite for Orthopedic Surgery," R.A. Casper, B.S. Kelley, R.L. Dunn, A.G. Potter and D.N. Ellis in *Polymeric Materials Science and Engineering*, Proceedings of the ACS Division of Polymeric Materials: Science and Engineering, vol. 53, Fall Meeting 1985.

"Totally Resorbable High–Strength Composite Material," by Benjamin S. Kelley, Richard L. Dunn and Robert A. Casper, *Advanced in Biomedical Polymers*, Edited by Charles G. Gebelein (1987).

"A View of Vascular Stents," by Richard A. Schatz, M.D. from the Arizona Heart Institute Foundation, Phoenix, Arizona (1988).

"Advances in Coronary Angioplasty: Endovascular Stents," by David W.M. Muller and Stephen G. Ellis, M.D. in *Coronary Artery Disease*, Jul/Aug 1990, vol. 1, No. 4.

"An Update on Coronary Stents," by Shing–Chiu Wong, M.D. and Richard A. Schatz, M.D. in *Cardio*, Feb. 1992.

*Primary Examiner*—Michael Powell Buiz
*Assistant Examiner*—Chalin Smith
*Attorney, Agent, or Firm*—Fulwider Patton Lee & Utecht, LLP

[57] ABSTRACT

An expandable sheath is provided for delivering a therapeutic drug in a body lumen which comprises an expandable membrane with a therapeutic drug incorporated therein. The expandable membrane is in a cylindrical configuration and mounted on the balloon portion of a catheter for intraluminal drug delivery into a patient's vascular system. The expandable membrane may also be mounted on an intravascular stent, both of which are implanted within the patient's vascular system. The therapeutic drug then diffuses into the vascular system at a controlled rate to match a specific clinical need.

8 Claims, 3 Drawing Sheets

U.S. PATENT DOCUMENTS

| | | |
|---|---|---|
| 5,062,829 | 11/1991 | Pryor et al. . |
| 5,084,065 | 1/1992 | Weldon et al. . |
| 5,085,629 | 2/1992 | Goldberg et al. . |
| 5,100,429 | 3/1992 | Sinofsky et al. ............ 606/195 |
| 5,108,370 | 4/1992 | Walinsky ..................... 604/96 |
| 5,108,755 | 4/1992 | Daniels et al. . |
| 5,151,105 | 9/1992 | Kwan-Gett . |
| 5,156,623 | 10/1992 | Hakamatsuka et al. . |
| 5,163,951 | 11/1992 | Pinchuk et al. . |
| 5,163,952 | 11/1992 | Froix . |
| 5,163,958 | 11/1992 | Pinchuk . |
| 5,192,311 | 3/1993 | King et al. . |
| 5,197,977 | 3/1993 | Hoffman, Jr. et al. . |
| 5,199,951 | 4/1993 | Spears ..................... 606/194 X |
| 5,234,456 | 4/1993 | Silvestrini ................ 606/194 |
| 5,234,457 | 8/1993 | Andersen . |
| 5,236,447 | 8/1993 | Kubo et al. . |
| 5,279,594 | 1/1994 | Jackson . |
| 5,282,860 | 2/1994 | Matsuno et al. . |
| 5,289,831 | 3/1994 | Bosley . |
| 5,290,271 | 3/1994 | Jernberg . |
| 5,306,286 | 4/1994 | Stack et al. . |
| 5,330,500 | 7/1994 | Song . |
| 5,342,348 | 8/1994 | Kaplan . |
| 5,356,433 | 10/1994 | Rowland et al. . |
| 5,383,927 | 1/1995 | De Goicoechea et al. . |
| 5,413,597 | 5/1995 | Krajicek ........................ 623/1 |
| 5,419,760 | 5/1995 | Narcisco, Jr. ............ 606/194 X |
| 5,439,446 | 8/1995 | Barry ..................... 606/194 X |
| 5,458,605 | 10/1995 | Klemm ..................... 606/108 |

DRUG LOADED ELASTIC MEMBRANE AND METHOD FOR DELIVERY

BACKGROUND OF THE INVENTION

1. Field of the Invention

This invention relates generally to the treatment of cardiovascular diseases such as restenosis, acute thrombosis, intimal hyperplasia and subacute thrombosis. More particularly, the invention relates to an expandable membrane containing a therapeutic drug for release into a body lumen for treating disease or injury.

2. Description of Related Art

Coronary devices have maintained unprecedented growth throughout the 1980's and 1990's such that coronary angioplasty is commonplace for treatment of atherosclerotic vascular disease. In a typical percutaneous transluminal coronary angioplasty (PTCA) procedure, a guiding catheter having a preformed distal tip is percutaneously introduced into the cardiovascular system through the brachial or femoral arteries and is advanced therein until the distal tip is in the ostium of the desired coronary artery. A guidewire and a dilatation catheter having an inflatable balloon on the distal end thereof are introduced through the guiding catheter with the guidewire slidably disposed within an inner lumen of the dilatation catheter. The guidewire is first advanced out of the distal end of the guiding catheter and is maneuvered into the patient's coronary vasculature containing the lesion to be dilated, and is then advanced beyond the lesion. Thereafter, the dilatation catheter is advanced over the guidewire until the dilatation balloon is located across the lesion. Once in position across the lesion, the balloon of the dilatation catheter is filled with radiopaque liquid at a relatively high pressure (e.g., greater than about four atmospheres) and is inflated to a predetermined size to radially compress the atherosclerotic plaque of the lesion against the inside of the arterial wall to thereby dilate the lumen of the artery. The balloon is then deflated so that the dilatation catheter can be removed and blood flow resumed through the dilated artery.

By way of example, further details of the angioplasty procedure and the devices used in such procedures can be found in U.S. Pat. No. 4,323,071 (Simpson-Robert); U.S. Pat. No. 4,439,185 (Lindquist); U.S. Pat. No. 4,516,972 (Samson); U.S. Pat. No. 4,538,622 (Samson et al.); U.S. Pat. No. 4,554,929 (Samson et al.); U.S. Pat. No. 4,616,652 (Simpson); U.S. Pat. No. 4,638,805 (Powell); and U.S. Pat. No. 4,748,982 (Horzewski et al.), which are hereby incorporated herein in their entirety by reference thereto.

A common problem that sometimes occurs after an angioplasty procedure is the appearance of restenosis at or near the site of the original stenosis in the blood vessel which requires a secondary angioplasty procedure or a bypass surgery. Numerous approaches developed during the late 1980's to treat restenosis of the coronary arteries in an attempt to decrease the incidence of acute complications and the chronic restenosis rate. For example, in the prior art are mechanical approaches such as atherectomy, stents, laser angioplasty, and the application of pharmacologic agents. Of the mechanical approaches described, only stents have been most promising to prevent restenosis and to prevent elastic recoil of the vascular wall.

In expandable stents that are delivered with expandable catheters, such as balloon catheters, the stents are positioned over the balloon portion of the catheter and are expanded from a reduced diameter to an enlarged diameter, greater than or equal to the diameter of the arterial wall, by inflating the balloon from within the stent. Stents of this type can be expanded to an enlarged diameter by deforming the stent and expanding it into engagement with the vascular wall. It is common for stents of this type to experience endothelial growth over and around the stent. Examples of such expandable catheters and stents are disclosed in U.S. Pat. No. 5,102,417 (Palmaz), U.S. Pat. No. 5,123,917 (Lee), and U.S. Pat. No. 5,133,732 (Wiktor), which are hereby incorporated herein in their entirety. Unfortunately, the stents that are currently being implanted are reported to have a fairly high restenosis rate, in the seven to forty percent range. With this relatively high restenosis rate, there has developed a need for some means of reducing the restenosis rate when using a stent, and limiting recurrent stenosis even when a stent is not used. The present invention fulfills this need.

SUMMARY OF THE INVENTION

The present invention is directed to an expandable membrane for use in delivering a therapeutic drug in a body lumen. One of the primary advantages of the invention is to provide local delivery of a therapeutic drug to eliminate the need for systemic delivery which may have undesirable side effects. Local delivery of a drug can be accomplished using a drug loaded expandable membrane carried by a perfusion-type catheter system (non-implantable) or by loading the membrane on a stent for implanting in a vessel. The drug release from the expandable membrane can be controlled to match a particular clinical need or specific condition such as restenosis or acute thrombosis.

The expandable sheath of the present invention comprises an expandable membrane in the form of a tubular or cylindrical member having a cavity for carrying a drug or which carries the drug in the form of a matrix. A therapeutic drug is loaded in the expandable membrane so that it can diffuse outwardly into the vessel wall once the expandable membrane is delivered to the site where a PTCA procedure has occurred. The expandable membrane is mounted on the distal end of a catheter, and more specifically on an expandable portion (balloon) by sliding or stretching the expandable membrane around the expandable portion of the catheter.

In one embodiment, the membrane may be in the form of a flat sheet with a first and second edge which overlap and are attached to each other so as to form a sleeve around the expandable portion of the catheter. In an alternative embodiment, the membrane is in the form of a seamless tube carried by the catheter. The catheter is then delivered intraluminally to the area where the diseased or injured area has occurred and the expandable portion of the catheter is expanded such that it also expands the expandable membrane. Once expanded, the therapeutic drug diffuses into the vessel wall for treating the injured or diseased area. Thereafter, the expandable portion of the catheter is deflated and the catheter and expandable membrane are withdrawn from the vasculature.

In another embodiment of the invention, the expandable membrane has a first layer and a second layer which are affixed to each other by sealing the edges of each layer. A cavity or reservoir is formed between the two layers for containing a therapeutic drug. Prior to attaching the two layers, the first elastic layer is stretched and drilled with a plurality of micro-holes or apertures through which the therapeutic drug can pass. Thereafter, the first layer and second layer are affixed to each other as described, and a therapeutic drug is injected into the cavity between the two layers through any of the plurality of apertures. When the expandable membrane is in its relaxed condition, the plurality of apertures close tightly so that no therapeutic drug can pass therethrough. The expandable membrane is then rolled onto the balloon portion of the catheter to form a cylindrical configuration and is delivered intraluminally as described above. The flat sheet is rolled into a cylinder and the edges are joined by welding, adhesive, etc. The balloon portion of the catheter is expanded thereby expanding the expandable membrane and forcing the therapeutic drug through the plurality of apertures and into contact with the vessel wall at the site of the injured or diseased area. After the therapeutic drug has been delivered, the balloon portion of the catheter is deflated and the catheter and expandable membrane are withdrawn from the vasculature. Instead of forming the expandable membrane from flat sheets, this embodiment may also be achieved with two tubular members, one within the other, to form a cavity between the layers. The ends are sealed and laser micro-holes are drilled into the outer layer to allow the therapeutic drug to pass therethrough. The tubular members also may have a drug incorporated in the polymer material in the form of a matrix which allows the drug to diffuse into the vessel wall over time.

In another embodiment of the invention, the expandable membrane is in the form of a flat sheet and having a thickness in the range of 0.002–0.020 inches. A plurality of micro-pockets are drilled into the outer surface of the expandable membrane, but are not drilled all the way through so as to form a hole. The micro-pockets are drilled while the membrane is in its stretched position. Thereafter, a therapeutic drug is loaded into the various micro-pockets and the membrane is relaxed so that the pockets close with the therapeutic drug inside. The elastic membrane can then be rolled into a cylindrical form and mounted on a catheter for delivery to the diseased or injured area. When the expandable membrane is expanded by the balloon portion of the catheter, the micro-pockets open and the therapeutic drug is delivered to the diseased or injured area. After the therapeutic drug has been delivered, the balloon portion of the catheter is deflated and the catheter and expandable membrane are withdrawn from the patient.

In yet another embodiment of the invention, an intravascular stent is mounted on the balloon portion of a catheter so that it may be implanted in a conventional manner within the vasculature. An expandable membrane having a therapeutic drug contained therein, in the form of a matrix, is mounted on the outer surface of the stent and the catheter, stent, and expandable membrane are delivered intraluminally to the injured or diseased area. As the balloon is expanded, it forces the stent radially outwardly along with the expandable membrane and into contact with the vessel wall. The balloon portion of the catheter is then deflated and the catheter and balloon withdrawn from the vasculature leaving the intravascular stent and expandable membrane implanted at the injured or diseased area. Thereafter, the therapeutic drug will diffuse from the matrix into the vessel wall to provide treatment in an effort to reduce the incidence of restenosis.

In both the reservoir or matrix form of drug delivery, the therapeutic drug may be retained in various structures including microspheres, sheets, tubes and so forth.

The expandable membrane of the present invention may be deployed in a body lumen through a variety of devices, including, but not limited to, balloon catheters and specialized devices which can deliver a stent within a body lumen. These and other advantages of the invention will become more apparent from the following detailed description thereof when taken in conjunction with the accompanying exemplary drawings.

DETAILED DESCRIPTION OF THE PREFERRED EMBODIMENTS

During PTCA procedures it is common to use a dilatation catheter to expand a diseased area to open the patient's lumen so that blood freely flows. Despite the beneficial aspects of PTCA procedures and its widespread and accepted use, it has several drawbacks, including restenosis and possibly acute thrombosis. This recurrent stenosis has been estimated to occur in seventeen to fifty percent of patients despite the initial PTCA procedure being successful. Restenosis is a complex and not fully understood biological response to injury of a vessel which results in chronic hyperplasia of the neointima. Intimal hyperplasia is activated by growth factors which are released in response to injury. Acute thrombosis is also a result of vascular injury and requires systemic antithrombotic drugs and possibly thrombolytics as well. This therapy can increase bleeding complications at the catheter insertion site and may result in a longer hospital stay. Another result of vessel injury is acute closure. It occurs in 3–5% of patents receiving a PTCA procedure and is caused by any one or all of three events, namely, thrombosis, vessel dissection, and/or elastic recoil.

Several procedures have developed to combat restenosis and acute closure, one of which is the delivery and implanting of an intravascular stent. Stents are in their developmental stage at this point and are being used in clinical trials throughout the United States and are regularly implanted in patients in Europe and other countries. Generally speaking, the stents can take numerous forms, however, it is generally a cylindrical hollow tube that holds open the vascular wall at the area that has been dilated by the dilatation catheter. The use of a stent does not always reduce restenosis and can aggravate the situation causing acute thrombosis, subacute thrombosis and intimal hyperplasia. In order to address the complications arising from PTCA procedures and the deployment of intravascular stents, the present invention for delivering therapeutic drugs was developed.

Figures 1, 2A, 2B, 3:
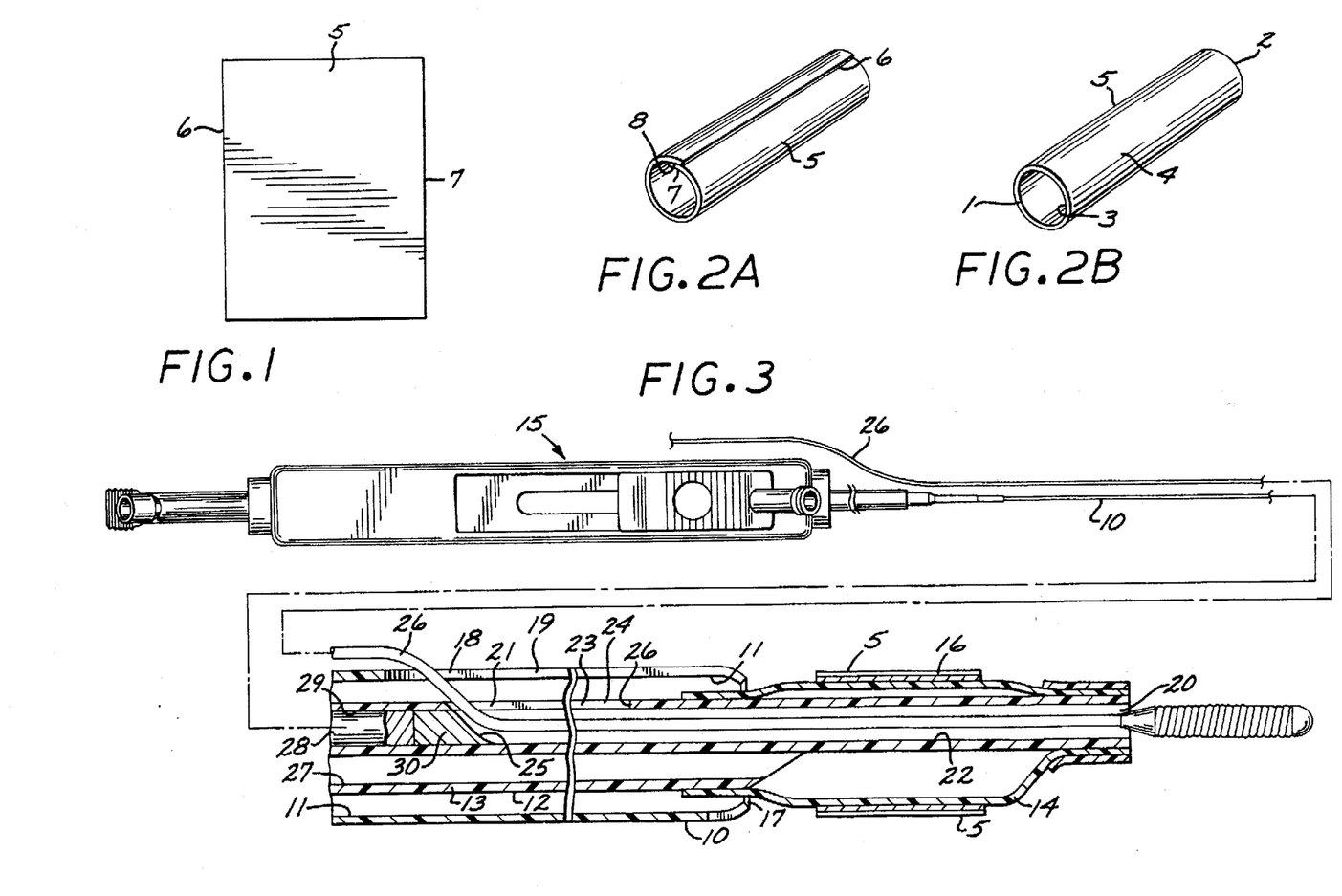
FIG. 1 is a top view of the expandable membrane of the invention prior to rolling into a cylindrical configuration.
FIG. 2A is a perspective view of the expandable membrane of FIG. 1 in its rolled up condition with its first edge attached to the second edge in an overlapping relationship.
FIG. 2B is a perspective view depicting the elastic membrane in a hollow tubular form that is seamless.
FIG. 3 depicts a partial cross-sectional view of an elevation of a rapid exchange catheter system having a stent mounted on a balloon with the expandable membrane mounted over the stent.

In one embodiment of the invention, and referring to FIGS. 1 and 2A, an elastic membrane 5 is depicted wherein it has a first edge 6 and a second edge 7. In FIG. 2A, elastic membrane 5 has been rolled into a cylindrical form with first edge 6 and second edge 7 attached in an overlapping relationship as depicted at point 8. It may be desirable to join first edge 6 and second edge 7 in an abutting relationship (not shown) rather than overlapping in order to reduce the overall profile.

In another preferred embodiment, as depicted in FIG. 2B, an elastic membrane 5 is depicted wherein it has a first end 1 and a second end 2 and is a substantially hollow cylinder. It further has an inner surface 3 and an outer surface 4 and is generally of a unitary nature. That is, it is formed from a continuous material and has no seams or overlapping edges. Various means are described below in which a therapeutic agent is incorporated within elastic membrane so that it may be delivered into a patient's vascular system for the purpose of diffusing the therapeutic agent at a controlled rate.

Expandable membrane 5 may be formed of any suitable material that is elastic and resilient. The material preferably is one that has a high degree of non-linearity (plastically deformable) for a wide range of stress and strain values (i.e., very low residual stress). In the preferred embodiment, however, any elastic material my be used. Commercially available tubing such as "C-Flex" tubing may be used. C-Flex may be obtained from Concept Polymer Technologies of Largo, Fla. In addition, the expandable material should have good tear strength to prevent fracturing or splitting when it is expanded and stretched. Other suitable properties for expandable membrane 5 include low modulus of elasticity, high toughness, a high percentage of elongation (at least 300%), and minimal residual stress after expansion. Several preferred materials for expandable membrane 5 are ethylene vinyl acetate (EVA) and biospan. Other suitable materials for expandable membrane 5 also include latexes, urethanes, polysiloxanes, and modified styrene-ethylene/butylene-styrene block copolymers (SEBS) and their associated families as well as elastomeric bioabsorbable materials from the linear aliphatic polyester group.

In keeping with the invention, a therapeutic drug is combined with the expandable membrane 5 for the purposes of diffusing the drug into the vessel wall of the patient. For this purpose any therapeutic drug for use in the body can be combined with the expandable membrane for treatment purposes. For example, therapeutic drugs for treating an injured or diseased area in a vessel and for combination with the expandable membrane can include antiplatelets, antithrombins, and antiproliferatives. Examples of antiplatelets and antithrombins include sodium heparin, LMW heparin, hirudin, hirulog, argatroban, forskolin, vapiprost, prostacyclin, dextran, D-phe-pro-arg-chloromethylketone (synthetic antithrombin), dipyridamole, glycoprotein IIb/IIIa platelet membrane receptor antibody, recombinant hirudin, thrombin inhibitor (from Biogen) and 7E-3B (antiplatelet drug from Centocor). Examples of antiproliferatives include angiopeptin (somatostatin analogue from a French company: Ibsen), angiotensin converting enzyme inhibitors (Captopril (Squibb), Cilazapril (Hoffman-LaRoche) and Lisinopril (Merk)), calcium channel blockers (Nifedipine), colchicine, fibroblast growth factor (FGF) antagonists, fish oil (omega 3-fatty acid), low molecular weight heparin (Wyeth, Glycomed), histamine antagonists, lovastatin (inhibitor of HMG-CoA reductase, cholesterol lowering drug from Merk), methotrexate, monoclonal antibodies (to PDGF receptors, etc.), nitroprusside, phosphodiesterase inhibitors, prostacyclin analogues, prostaglandin inhibitor (Glaxo), seramin (PDGF antagonist), serotonin blockers, steroids, thioprotease inhibitors, triazolopyrimidine (PDGF antagonist from Japanese company). While the foregoing therapeutic agents have been used to prevent or treat restenosis and thrombosis, they are provided by way of example and not meant to be limiting, as other therapeutic drugs may be developed which are equally applicable for use with the present invention.

In keeping with the invention, the therapeutic drug is combined with expandable membrane 5 by one of several methods. The therapeutic drug can be loaded into the expandable membrane by known methods such as melt processing, solvent casting, injection molding, extrusion, coating or by diffusion/absorption techniques. Other methods of incorporating a drug into a polymeric material are well known and include heating processes. Such processes must be carefully monitored and controlled at temperatures that are low enough to prevent degrading the drug. It is important that the therapeutic drug be able to diffuse out of expandable membrane 5 and into the patient's vascular system at a controlled rate once the expandable membrane is delivered to the injured or diseased area. Thus, the rate of diffusion is controlled to fit the circumstances and can range from a very rapid diffusion to a long term diffusion rate.

Figure 4A:
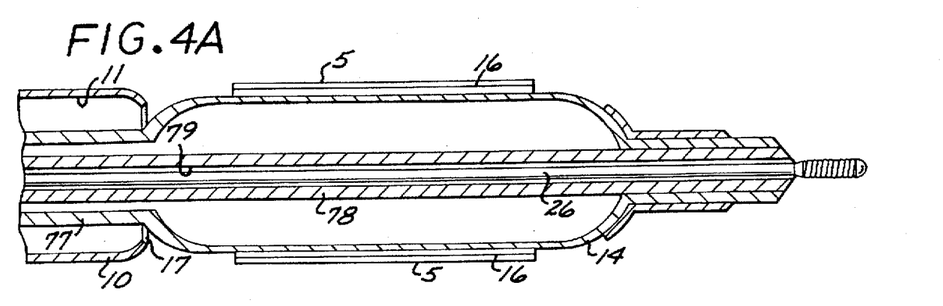
FIG. 4A is a partial cross-sectional view depicting an over-the-wire catheter system having a stent mounted on the balloon portion of the catheter and an expandable membrane mounted over the stent.
Figure 4B:
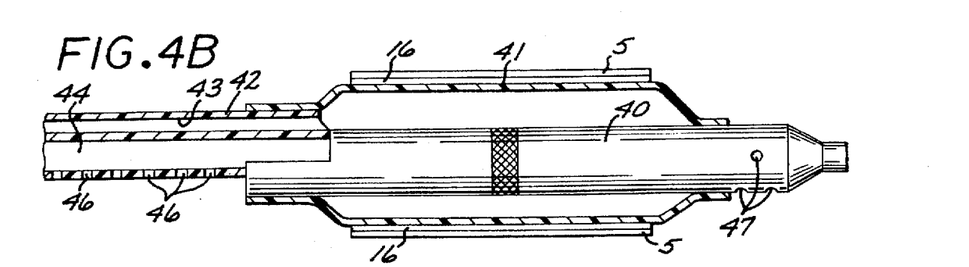
FIG. 4B is a partial cross-sectional view of a perfusion-type catheter system having a stent mounted on the balloon portion of the catheter and an expandable membrane over the stent.
Figure 5:
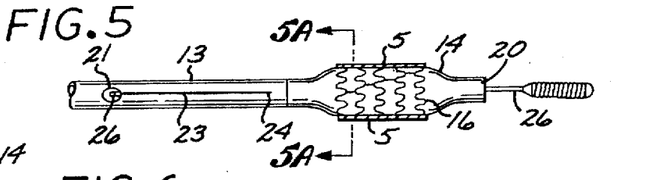
FIG. 5 is an elevational view depicting the rapid exchange catheter system of FIG. 3 wherein the stent mounted on the balloon portion of the catheter has a specific configuration and the expandable membrane is mounted over the stent.
Figure 5A:
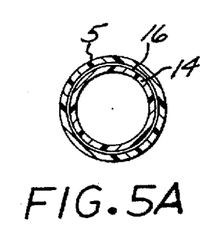
FIG. 5A is a cross-sectional view taken along line 5A—5A depicting the expandable membrane over the stent and balloon portion of the catheter.

Generally speaking expandable membrane 5 can be delivered within a patient's vascular system by any catheter system such as commonly and well known dilatation catheters having balloon portions at their distal tips. There are a wide range of catheter systems available, three of which are depicted in FIGS. 3, 4A and 4B. In FIG. 3 a rapid exchange catheter system is depicted, in FIG. 4A an over-the-wire system is depicted and in FIG. 4B a perfusion catheter is depicted. For purposes of the present invention, however, any of these systems suffice and numerous other catheter systems would be appropriate, including dilatation catheters. Typical dilatation catheter and perfusion balloon catheter systems can be found in U.S. Pat. Nos. 4,323,071; 4,516,972; 5,061,273; 5,137,513; 5,195,971, which are incorporated herein by reference. An advantage to using a perfusion balloon catheter system is that the balloon can remain inflated for longer periods of time since it allows blood flow to continue past the inflated balloon.

While expandable membrane 5 can be mounted directly to the balloon portion of a catheter for intraluminal delivery, the preferred embodiment is to deploy expandable membrane 5 in the patient's vascular system using an intravascular stent. Thus, FIGS. 4A, 4B, 5 and 5A illustrate a stent delivery system which embodies features of the invention for implanting expandable membrane 5.

Referring to FIG. 3, the rapid exchange delivery system includes a delivery sheath 10 which has an outer lumen 11 and an intravascular catheter 12 disposed within the outer lumen 11. The intravascular catheter has an elongated catheter body 13 and a balloon 14 on the distal portion of the catheter body. A manipulating device 15 is provided on the distal end of the delivery system which is employed to affect relative axial or longitudinal movement between the delivery sheath 10 and the intravascular catheter 12. An expandable stent 16, which is to be delivered and implanted within a patient's body lumen, is mounted on the exterior of the balloon 14. The stent disclosed in U.S. Ser. No. 08/164,986, which is commonly assigned, is suitable for use with the present invention. Such stents are expandable and deform beyond their elastic limit to hold open the vessel wall in which they are implanted.

The delivery sheath 10 has a distal port 17 in its distal end which is in fluid communication with the outer lumen 11 and a proximal port 18 disposed proximally to the distal port. The distal portion of delivery sheath 10 tapers down in a spherical-like manner so that the cross-sectional area is somewhat less in the distal region than the cross-sectional area of the rest of the delivery sheath. A slit 19 extends from the proximal port 18 to a location just proximal to the distal port 17.

The intravascular catheter 12 has a distal port 20 and a proximal port 21 which are in fluid communication with a first inner lumen 22 extending within the distal portion of the catheter 12 and being adapted to slidably receive a guidewire therein. A slit 23 extends from the proximal port 21 to a location 24 proximal to the proximal end of balloon 14. The proximal end of the guidewire receiving first inner lumen 22 is provided with a ramp 25 to guide the proximal end of guidewire 26 out of the proximal port 21 of intravascular catheter 12 when the catheter is mounted onto the guidewire, as will be discussed hereinafter. A second, much longer inner lumen 27 is provided within the catheter body 13 to direct inflation fluid from the proximal end of the catheter body to the interior of balloon 14.

Proximal to the proximal port 21 in catheter body 13 is a stiffening member 28 which is disposed in third inner lumen 29 provided within catheter body 13. As shown in the drawings, third inner lumen 29 and first inner lumen 22 may be the same lumen with a plug 30 separating the two lumens. The ramp 25 is on the distal side of plug 30.

Figure 6:
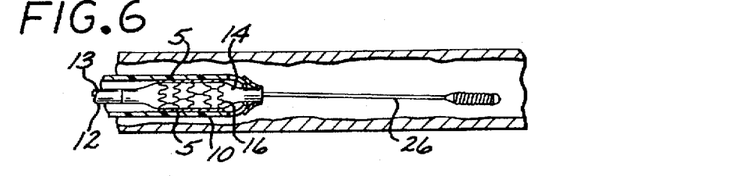
FIG. 6 is a partial cross-sectional view of the catheter delivery system and stent with the membrane mounted on the stent being transluminally delivered within the patient's vasculature.

In a typical stent deployment, expandable membrane 5 is loaded onto stent 16 so that it covers the stent without overlapping the ends of the stent. The expandable membrane and intravascular stent will be implanted in a patient's vascular system to treat the diseased and injured area and to allow sufficient blood flow through the vessel. Thus, as depicted in FIGS. 5–8 (including FIGS. 5A and 8A), intravascular stent 16 and expandable membrane 5 are implanted in the patient's vascular system. Typically, in these situations there will usually be a guidewire 26 (or other guiding member) which extends across the damaged section of the artery such as shown in FIG. 6. The proximal end of guidewire 26, which extends out of the patient during the entire procedure is inserted through the distal port 20 in the distal end of catheter 12 and advanced proximally through first inner lumen 22 until the proximal end of the guidewire impacts the ramp 25 and is thereby directed through the proximal port 21.

Figure 7:
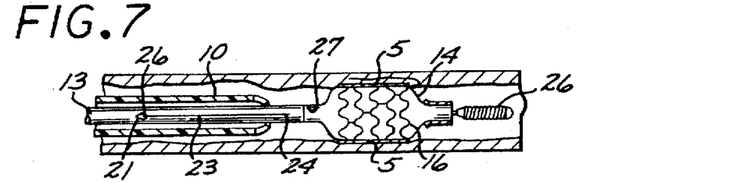
FIG. 7 is a partial cross-sectional view of the balloon portion of the catheter expanding the stent and the expandable membrane within the patient's vasculature.
Figure 8:
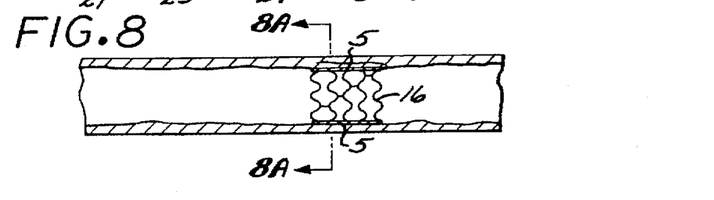
FIG. 8 is a partial cross-sectional view of an intravascular stent and an expandable membrane implanted against the patient's vessel wall.
Figure 8A:
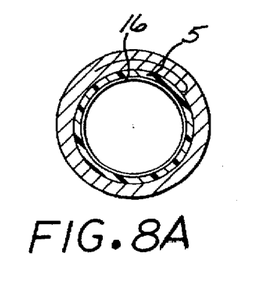
FIG. 8A is a cross-sectional view taken along line 8A—8A depicting the expandable membrane and stent expanded and in contact with the vessel wall.

The intravascular catheter 12 is preferably positioned within outer lumen 11 of the delivery sheath 10 so that at least a significant portion of the proximal port 18 in the sheath is in alignment with the proximal port 21 of the intravascular catheter. In this manner, proximal advancement of the guidewire 26 through the inner lumen 22 will also direct the proximal end of the guidewire out the proximal port 18 in the delivery sheath. The proximal end of the guidewire 26 may then be manually held to maintain the position of the guidewire within the patient's vasculature, while the stent delivery system is advanced over the guidewire and through the patient's vascular system. The advancement of the stent delivery system with expandable membrane 5 mounted thereon continues until the distal ends of the catheter and sheath extend adjacent to or across the injured or diseased area. Next, the manipulator 15 on the proximal end of the delivery system is actuated to move sheath 10 proximally with respect to the catheter 12 and thereby expose stent 16 and expandable member 5 which are mounted on balloon 14. Thereafter, inflation fluid is directed under substantial pressure through inflation lumen 27 in the catheter body 13 to the interior of balloon 14, thereby expanding the balloon and simultaneously expanding stent 16 and expandable member 5 against the vessel wall as shown in FIG. 7. After balloon 14 is deflated, the delivery systems, both sheath 10 and catheter 12, are then removed from the patient along with guidewire 26, leaving the expanded stent 16 pressing against expandable member 5 which is in contact with the vessel wall as is shown in FIGS. 8 and 8A.

The therapeutic drug contained within expandable membrane 5 can then diffuse directly into the vessel wall at the area of the injured or diseased vessel to provide treatment.

In another embodiment of the invention, as depicted in FIG. 4A, an over-the-wire catheter system is employed to carry the stent 16 and expandable membrane 5 within the patient's vasculature to the damaged area. A guidewire 26 is employed to cross a damaged area and locate the position within the patient so that the intravascular catheter can reach the diseased or injured area. As is typical in over-the-wire catheter systems, the intravascular catheter has an outer member 77 and an inner member 78 which are coaxially aligned. Inner member 78 has an inner lumen 79 which carries guidewire 26. The guidewire can move freely within inner lumen 79 in an axial direction. The intravascular catheter is slidably disposed within sheath 10 in inner lumen 11. Port 17 at the distal end of sheath 10 provides an opening for the catheter to extend.

The method of deploying expandable membrane 5 is similar to that described for the rapid exchange system described above and as depicted in FIGS. 3, 5–8, and 5A and 8A. Generally, guidewire 26 is positioned at a location just past the injured or diseased area and the catheter system is threaded over guidewire 26 so that balloon 14, along with stent 16 and expandable membrane 5 are positioned at the injured or diseased area. Thereafter, balloon 14 is expanded radially outwardly to thereby expand stent 16 and expandable membrane 5. Expandable membrane 5 is sandwiched between the patient's vasculature and stent 16. Balloon 14 is then deflated and the catheter system is withdrawn from the patient's vasculature leaving stent 16 and expandable membrane 5 securely implanted in the injured or diseased area. The therapeutic drugs within expandable membrane 5 then diffuse into the patient's vessel wall to treat the injured or diseased area.

Expandable membrane 5 also can be delivered intraluminally by loading it onto a perfusion-type dilatation catheter of the type disclosed in U.S. Pat. No. 5,195,971 (Sirhan) and as depicted in FIG. 4B. One advantage in using a perfusion catheter is that blood continues to flow on both sides of the inflated balloon thereby allowing longer balloon inflation times. Thus, as shown in FIG. 4B, expandable membrane 5 may be loaded directly onto balloon 41 or onto a stent carried by the balloon. Balloon 41 is mounted on tubular extension 40 which is carried by the perfusion catheter. The proximal end of balloon 41 is attached to distal section 42. The perfusion catheter has an inflation lumen 43 and a guidewire lumen 44. Inflation lumen 43 will carry inflation fluid to expand balloon 41 and expandable membrane 5. Guidewire lumen 44 will receive a guidewire (not shown) similar to that depicted in FIG. 4A. In order to permit blood to flow continuously while balloon 41 is expanded, a plurality of perfusion ports are incorporated. Thus, proximal perfusion ports 46 and distal perfusion ports 47 permit blood to flow through guidewire lumen 44 while balloon 41 and expandable membrane 5 are in their expanded condition. Intraluminal delivery and implanting are similar to that described for the over-the-wire catheter of FIG. 4A. By using a perfusion-type catheter system, expandable membrane 5 does not have to be implanted because it can be delivered and expanded into contact with the vessel wall for long periods of time without adverse effects to the patient. When the drug has diffused, the perfusion balloon is deflated and elastic membrane 5 elastically contracts along with the deflated balloon. The entire catheter system and elastic membrane 5 are then removed from the patient.

Figure 9:
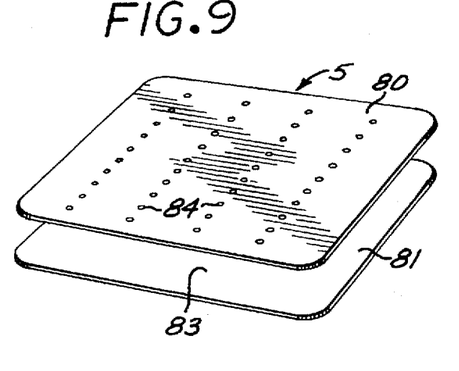
FIG. 9 is a perspective view of the expandable membrane wherein the first layer and the second layer are spaced apart prior to affixing the edges to each other.
Figure 10:
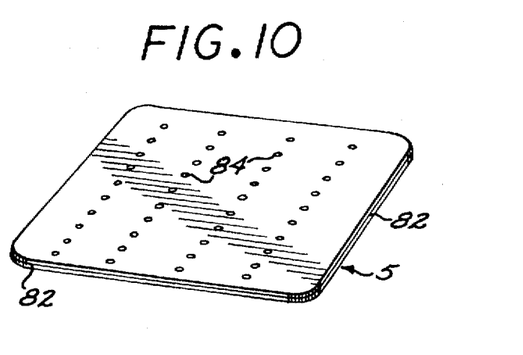
FIG. 10 is the expandable membrane of FIG. 9 wherein the first layer and the second layer have been joined and the plurality of holes are closed since the membrane is in its relaxed condition.

In another embodiment of the invention, as depicted in FIGS. 9 and 10, expandable membrane 5 has a first layer 80 and second layer 81 spaced apart. First layer 80 and second layer 81 are then joined along their edges to form a fluid-tight seal 82 along all of their edges. Both first layer 80 and second layer 81 can be formed from any of the expandable and elastic materials described above with respect to the elastic membrane depicted in FIG. 1.

Before joining first layer 80 to second layer 81, a plurality of apertures 84 (holes) are formed in first layer 80 by known methods, such as using a laser or other methods for making micro-holes in an elastic membrane. Holes 84 are formed in a first layer 80 while it is in stretched condition so that when first layer 80 is in a relaxed condition the holes will close to form a fluid-tight seal.

Figure 11:
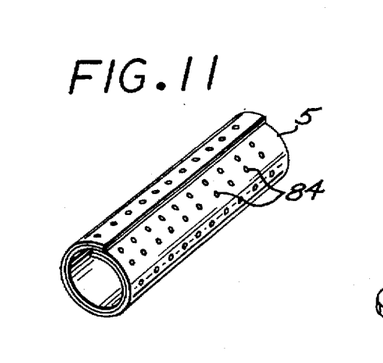
FIG. 11 is a perspective view of the expandable membrane of FIG. 10 in its rolled up condition and in an unexpanded state with the plurality of micro-holes tightly closed thereby containing the drug within the drug filled reservoir.

Once first layer 80 and second layer 81 have been joined together, they are stretched and a therapeutic drug is injected through any of holes 84 to fill cavity 83 which is formed between the two joined layers. After the therapeutic drug is injected into cavity 83, the expandable membrane is relaxed and holes 84 will then close so that the therapeutic drug is contained within. Expandable membrane 5 as depicted in FIG. 11 is now ready for rolling into a cylindrical configuration. It also may be desirable to roll the membrane so that the edges abut rather than overlap so that the cylindrical shape has a lower profile.

Delivery of the expandable membrane 5 of FIG. 11 is similar to that described for the expandable membrane of FIGS. 1, 2A and 2B. Again referring to the expandable membrane of FIG. 11, it can be mounted on a stent which is mounted on the balloon portion of the catheter. Thereafter, the catheter, along with the expandable membrane and stent, is delivered intraluminally as described above. Unlike the prior description relating to the expandable membrane of FIGS. 2A and 2B, expanding the expandable membrane 5 of FIG. 11 will force the therapeutic drug through holes 84 when the expandable membrane is expanded by balloon 14 and stent 16 on which it is mounted. Thus, as expandable membrane 5 gets larger, holes 84 begin to open allowing the diffusion of the therapeutic drug into the patient's vessel wall. As the balloon expands stent 16 expands radially outwardly and it increases the pressure on expandable membrane 5 and causes yet more of the therapeutic drug to diffuse outwardly into the patient's vessel wall. Expandable membrane 5 is then sandwiched between the vessel wall and stent 16 when balloon 14 is fully expanded and the stent is implanted against the vessel wall. Thus, the therapeutic drug is injected at the injured or diseased area to provide maximum treatment at the specific site. The invention eliminates systemic levels of drugs which may well result in negative (undesirable) side effects such as bleeding complications and toxicity. The polymer sleeve may also be loaded in matrix format to allow for sustained release of the same or a different drug.

Figure 11A:
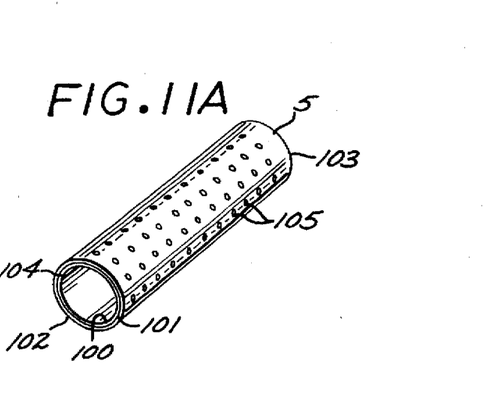
FIG. 11A is a perspective view of an expandable membrane having an inner tube and an outer tube with a drug receiving cavity in between the two tubes.

In another embodiment of the invention, as depicted in FIG. 11A, a pair of seamless cylindrical tubes, concentrically aligned, form expandable membrane 5. An inner tubular member 100 is surrounded by an outer tubular member 101 and the ends 102,103 are sealed by any known method such as welding or by adhesives. A reservoir 104 is formed between inner and outer tubular members 100,101 for receiving a therapeutic drug. A plurality of micro-holes 105 are formed in outer tubular member 101 by a laser or other known method. While expandable membrane 5 is in a stretched condition, the therapeutic drug is injected into reservoir 104 through micro-holes 105, and thereafter expandable membrane 5 is relaxed thereby closing micro-holes 105 and trapping the therapeutic drug in reservoir 104. The expandable membrane 5 of FIG. 11A can then be loaded onto a stent 16 and implanted against a vessel wall in the same manner as previously described for FIG. 11. Once expandable membrane 5 is expanded, the therapeutic drug is injected through micro-holes 105 directly into the vessel wall.

It should be understood that with all of the embodiments described herein, expandable membrane 5 can also carry one or more therapeutic drugs in a matrix format. For example, again referring to FIG. 11A, inner and outer tubular members 100,101 each may be loaded with one or more therapeutic drugs in a matrix form. When expandable membrane 5 is implanted as described above, the therapeutic drug(s) contained in the matrix will release into the vessel wall at a predetermined rate. The therapeutic drug in reservoir 104, however, will be injected into the vessel wall rapidly as previously described. Thus, by providing a combination of drugs within reservoir 104 and in matrix form in inner and outer tubular members 100,101, drugs are continuously administered at a specific site over a long period of time. For example, inner tubular member 100 can be loaded with a sustained released antithrombotic drug since the inner tubular member is in direct contact with blood flow. The outer tubular member 101, which is pressed against the vessel wall, is loaded with a sustained release antiproliferative drug. Depending on the drug and the polymer used, in excess of 40% by weight of a drug can be loaded into the tubular members 100,101.

Figure 12:
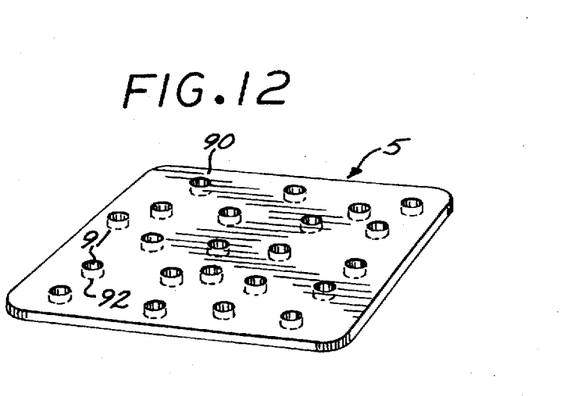
FIG. 12 is a perspective view of the expandable membrane having a plurality of micro-pockets for receiving a therapeutic drug.
Figure 13:
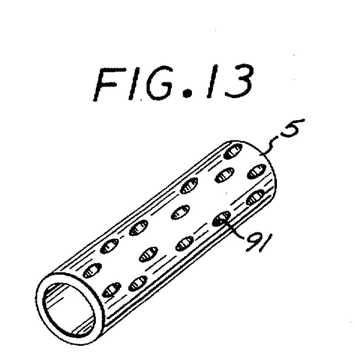
FIG. 13 is a perspective view of the expandable membrane of FIG. 12 in its rolled up condition in a cylindrical form with the micro-pockets tightly closed and in an unexpanded condition.

In another embodiment of the invention, as depicted at FIGS. 12 and 13, expandable membrane 5 is substantially thicker than previously described, and on the order of 0.010–0.050 inches. In this embodiment, an elastic sheet 90 contains a plurality of micro-pockets 91 which have a depth of several millimeters, but do not extend entirely through sheet 90. Thus, micro-pockets 91 each have a bottom 92 and are hollow for receiving a therapeutic drug. Micro-pockets 91 can be formed by laser drilling or conventional drilling while expandable membrane 5 is in a stretched condition, as depicted in FIG. 12. Thereafter, the expandable membrane 5 is relaxed and the micro-pockets 91 close tightly thereby containing the therapeutic drug therein. As depicted in FIG. 13, sheet 90 is rolled into a cylindrical form so that it may be delivered intraluminally in the same manner as the expandable membrane depicted in FIGS. 9–11. In the preferred form, the micro-pockets 91 are filled with a therapeutic drug in the form of microspheres as described herein. Micro-pockets 91 (FIG. 13) may be covered with a thin film that will act as a rate limiting membrane (not shown). Such rate limiting membranes are well known and can be of the perfusion membrane type, or a hydrophilic coating that dissolves quickly upon exposure to the patient's vessel. Commonly known hydrophilic coatings include hydrogel, glucose, acetate, agar and starch. Until expandable membrane 5 is expanded, the therapeutic drug in micro-pockets 91 is sealed in by the rate limiting membrane. Upon expansion of membrane 5, the drug diffuses from micro-pockets 91 through the rate limiting membrane at a predetermined rate. The rate limiting membrane can be laminated to sheet 90 as herein described.

The expandable membrane 5 depicted in FIG. 12 need not be formed solely from a flat sheet but also can be formed from a seamless tubular member similar to that shown in FIG. 2B. In this embodiment as well as with FIGS. 12–13, a therapeutic drug can be in the form of a matrix combined with the polymer comprising expandable membrane 5. By loading the drug into matrix form, the time during which the drug diffuses into the vessel wall can be controlled to allow for various stages of disease treatment and recovery. Further, multiple drugs in the matrix can be diffused at rates that coordinate with the particular injury or disease to provide optimal treatment. The matrix can be dispersed in expandable membrane 5 by known methods including solvent casting, coating, absorption or melt processing.

Membrane 5 as described herein can also be made from bioabsorbable materials which will completely absorb into the patient's vascular system over time. Membrane 5 can be made from members or co-members of the linear aliphatic polyester family, polyurethanes, and composites.

The dimensions of the intravascular catheter described herein will generally follow the dimensions of intravascular catheters used in angioplasty procedures in the same arterial location. Typically, the length of a catheter for use in the coronary arteries is about 150 cm, the outer diameter of the catheter shaft is about 0.035 inch (0.89 mm), the length of the balloon is typically about 2 cm, and the inflated diameter is approximately 1 to about 8 mm.

The materials of construction may be selected from those used in conventional balloon angioplasty catheters, such as those described in the patent incorporated herein by reference. The delivery sheath will generally be slightly shorter than the intravascular catheter, e.g., by about the length of the manipulating device 15, with an inner diameter large enough to accommodate the intravascular catheter and to allow the catheter free longitudinal movement therein. The sheath and the catheter shaft can be made of conventional polyethylene tubing, or any other material as described in the catheter patents incorporated herein by reference.

While the present invention has been described herein in terms of delivering an expandable membrane and intravascular stent to a desired location within a patient's vascular system the delivery system can be employed to deliver expandable membranes and/or stents to locations within other body lumens such as peripheral arteries and vessels, the urethra, or fallopian tubes, so that the stents can be expanded to maintain the patency of these body lumens. Other areas for implanting an expandable membrane could be iliac arteries, the aorta, or virtually any other body lumen. Various changes and improvements may also be made to the invention without departing from the scope and spirit thereof.

What is claimed is:

1. An expandable sheath for delivering a therapeutic drug in a body lumen, comprising:

an expandable membrane in the form of a cylindrical member and having a first end and a second end;

a therapeutic drug combined with said expandable membrane;

means for intraluminally delivering and expanding said expandable membrane in the body lumen so that said therapeutic drug can be eluted at a specific site in the body lumen;

said expandable membrane further comprises a first layer and a second layer, said first layer and said second layer are bonded together along their edges to form a reservoir between the two layers;

a plurality of apertures formed in said first layer by a laser when said expandable membrane is in a stretched condition;

said therapeutic drug is loaded into said reservoir through said apertures when said membrane is in said stretched condition; and said expandable membrane retains said therapeutic drug within said reservoir when said membrane is in a relaxed condition; whereby said membrane is rolled into a cylinder so that said first edge and said second edge overlap and are attached to each other.

2. The expandable sheath of claim 1, wherein said membrane is rolled into a cylinder so that said first edge and said second edge abut and are attached to each other.

3. The expandable sheath of claim 1, wherein said expandable membrane is attached to a balloon portion of a catheter for intravascular transport and delivery to a specific site in the body lumen.

4. The expandable sheath of claim 3, wherein said balloon portion of said catheter expands, thereby expanding said expandable membrane and forcing said therapeutic drug in said reservoir to diffuse through said apertures and into the lumen wall.

5. An expandable sheath for delivering a therapeutic drug in a body lumen, comprising:

an expandable membrane having a first layer and a second layer, said first layer and said second layer affixed to each other along their edges to form a drug-containing reservoir between the two layers;

a plurality of apertures on said first layer through which the therapeutic drug can diffuse from within said drug-containing reservoir, said plurality of apertures remaining open when said first layer is in a stretched condition and said apertures tightly closing when said first layer is in a relaxed condition; and a catheter having a proximal end and a distal end, the catheter further having an expandable balloon portion at the distal end and an intravascular stent mounted thereon, said expandable membrane is affixed to said stent by rolling said expandable membrane to form a cylinder around said intravascular stent.

6. The expandable sheath of claim 5, wherein said expandable balloon is expanded from a first diameter to a second enlarged diameter thereby expanding said stent and said expandable membrane so that said stent and said expandable membrane are implanted in the body lumen.

7. The expandable sheath of claim 6, wherein said plurality of apertures on said first layer open when said expandable membrane is expanded by said expandable balloon and intravascular stent, so that as said plurality of apertures open the therapeutic drug will diffuse from within said drug-containing reservoir to said body lumen.

8. An expandable sheath for delivering a therapeutic drug in a body lumen, comprising:

an expandable membrane having a first layer and a second layer, said first layer and said second layer affixed to each other along their edges to form a drug-containing reservoir between the two layers;

a plurality of apertures on said first layer through which the therapeutic drug can diffuse from within said drug-containing reservoir, said plurality of apertures remaining open when said first layer is in a stretched condition and said apertures tightly closing when said first layer is in a relaxed condition; and a catheter having a proximal end and a distal end, the catheter further having an expandable balloon portion at its distal end and an intravascular stent mounted thereon, said expandable membrane is affixed to said stent by rolling said expandable membrane to form a cylinder around said intravascular stent;

said second layer has an inner surface in contact with blood flow, said inner surface loaded with a sustained release antithrombotic drug for diffusing into the blood at a predetermined rate.

* * * * *